United States Patent [19]

Hess et al.

[11] Patent Number: 4,670,467

[45] Date of Patent: Jun. 2, 1987

[54] METHOD OF CONTROLLING GRAFT VERSUS HOST REACTION

[75] Inventors: Richard A. Hess, Bethesda; Donald P. Tschudy, Chevy Chase, both of Md.

[73] Assignee: The United States of America as represented by the Secretary of the Department of Health and Human Services, Washington, D.C.

[21] Appl. No.: 792,836

[22] Filed: Oct. 30, 1985

[51] Int. Cl.⁴ ............................................. A61K 31/19
[52] U.S. Cl. .................................. 514/557; 514/574; 514/885
[58] Field of Search ................................. 514/557, 574

[56] References Cited

PUBLICATIONS

Chemical Abstracts 98:191394n (1983).
Tschudy et al., J. Lab. and Clin. Med. 99:526–632 (1982).
Tschudy et al., Oncology 40:148–154 (1983).
Pendarvis et al., J. Org. Chem. 39:2289–2291 (1974).
Ebert et al., Biochemical and Biophysical Research Communications 88:1382–1390 (1979).

*Primary Examiner*—Leonard Schenkman
*Attorney, Agent, or Firm*—Holman & Stern

[57] ABSTRACT

The present invention discloses a method of controlling graft versus host disease, resulting from bone marrow transplantation by treating the host with succinylacetone. A dosage of about 800 mg/kg body weight every 4 days is found optimal.

5 Claims, 3 Drawing Figures

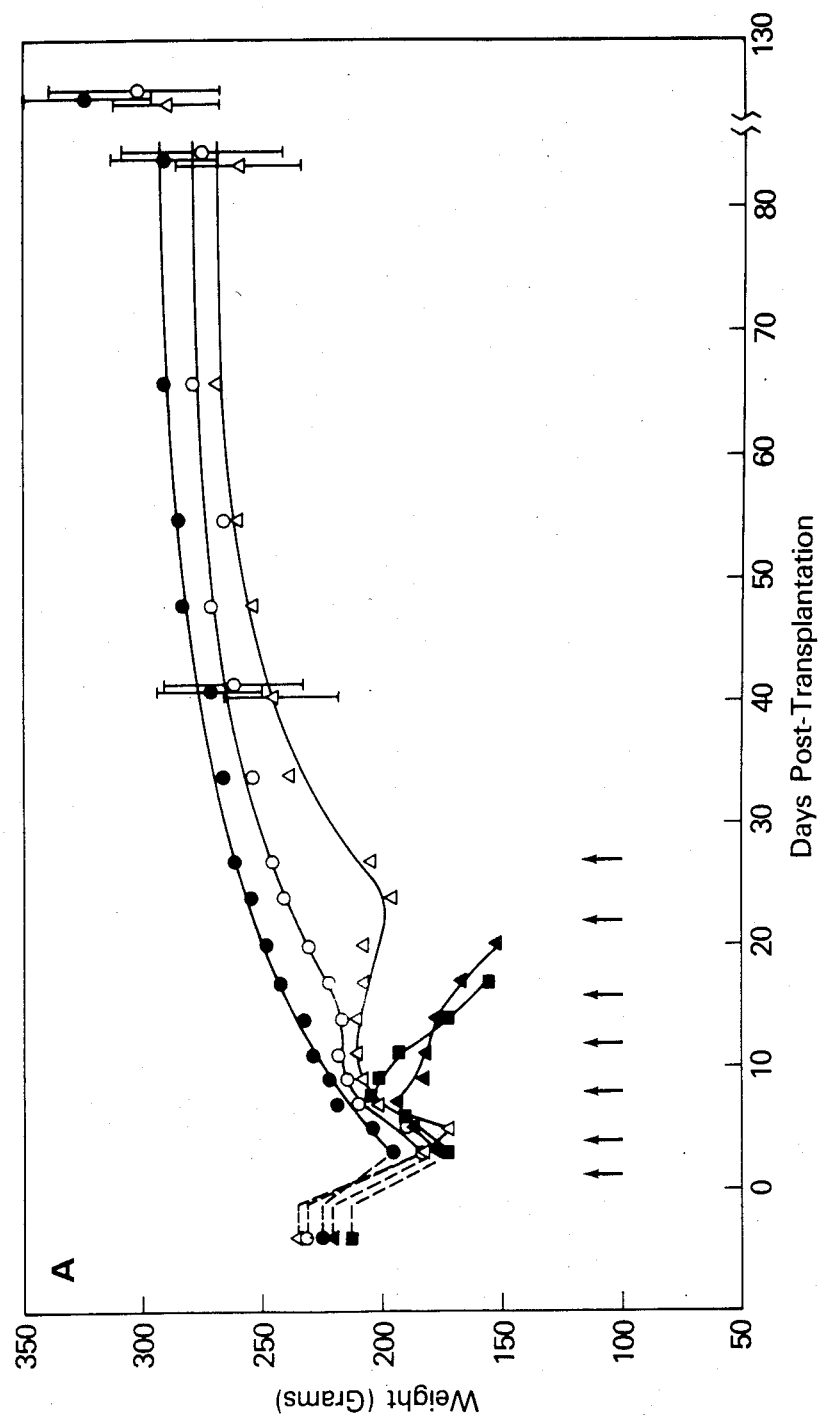

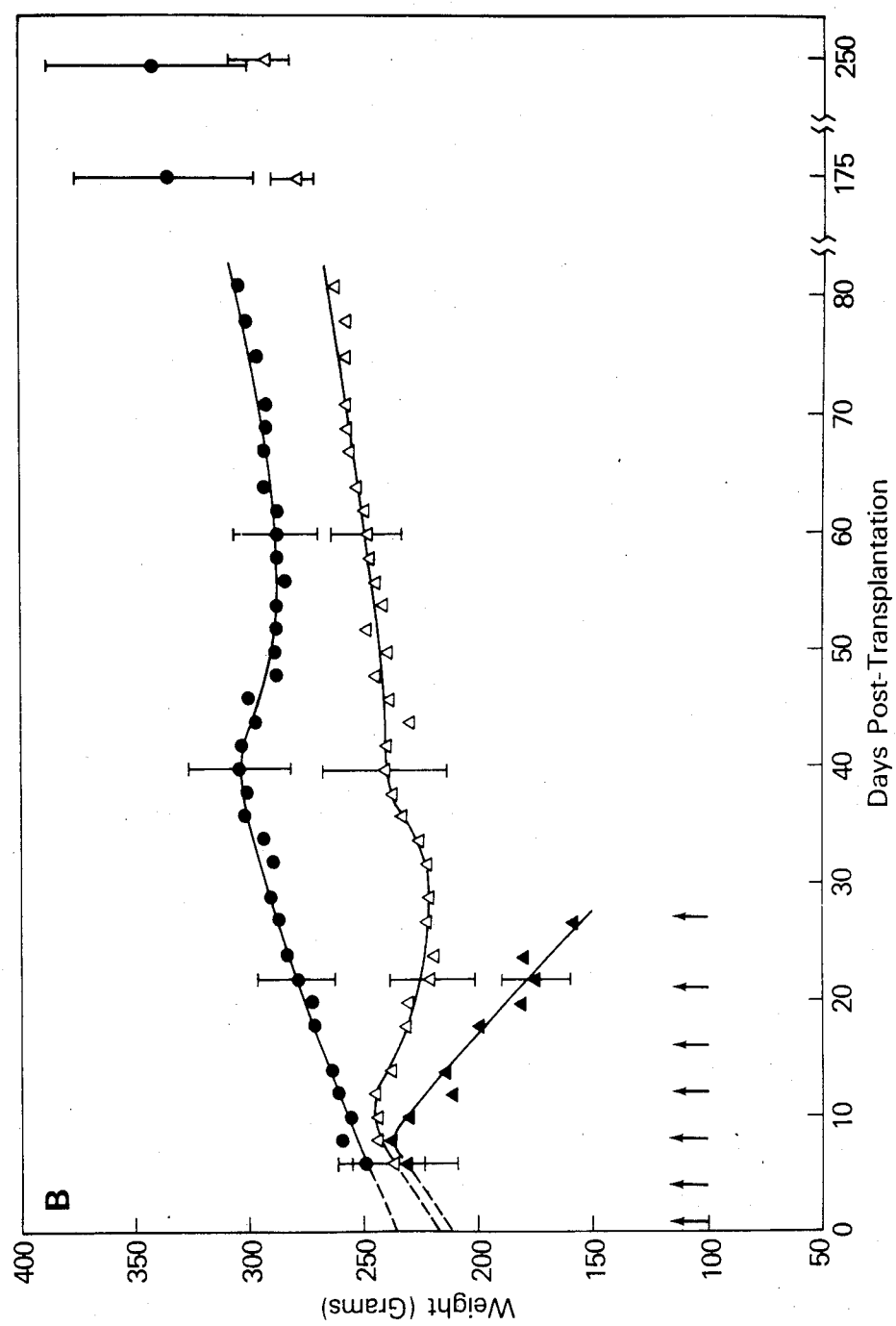
FIG. 2 PANEL B

METHOD OF CONTROLLING GRAFT VERSUS HOST REACTION

BACKGROUND OF THE INVENTION

1. Technical Field

The present invention is related to a method of controlling graft versus host reaction. More particularly, the present invention is related to the prevention or amelioration of graft versus host disease (GVHD) in bone marrow transplantation by succinylacetone (SA).

2. State of the Art

Successful bone marrow transplantation has wide application to a variety of serious diseases ranging from leukemia to radiation caused illness. Efficacy of bone marrow transplantation in the treatment of a number of human disorders is a subject of active investigation for such conditions as severe combined immunologic deficiency, aplastic anemia, genetic disorders of the marrow such as thalassemia major and malignant disorders, including acute leukemia (relapsed once), acute non-lymphocytic leukemia in first remission, chronic granulocytic leukemia and the like. Since donor and recipient are rarely genetically identical, some degree of histocompatability antigen mismatch is inevitable in most bone marrow transplants. Even where donors and recipients are HLA matched, that is, matched for the antigens of the major histocompatability complex (MHC) loci, problems can arise from mismatched minor loci.

The most serious problem which occurs in allogeneic bone marrow transplants is the development of graft versus host disease (GVHD). In the recipient whose capacity for immune rejection of the allogeneic transplant is genetically deficient or has been eliminated by means of radiation and/or cytotoxic drugs, the immunocompetent cells in the graft can recognize foreign antigens in the recipient and attack various tissues (gastrointestinal tract, skin, lymphoid organs and liver), leading to acute GVHD and a fatal outcome in some patients. Furthermore, GVHD can occur in a chronic form which can also be fatal. Management of this problem involves both prophylaxis and treatment of the actual disease. It has been reported that despite methotrexate prophylaxis for the first 100 days, 35-50% of treated patients still developed GVHD, and similar results have been reported with cyclophosphamide and cyclosporin A. These values are for the condition where the donor and recipient are HLA matched. The incidence of GVHD approaches 100% for HLA mismatched donor-recipient combinations. Therefore, GVHD severely limits the use of bone marrow transplantation to HLA matched donor recipient combinations. Thus, there is a great need for better agents for the prophylaxis and control of GVHD.

Succinylacetone (SA, 4,6-dioxoheptanoic acid) was discovered in the urine of patients with hereditary tyrosinemia (Linddblad, et al., 1977. Proc. Natl. Acad. Sci. USA, 74:4641-4645). It is an inhibitor of δ-aminolevlinic acid dehydrase (Tschudy, et al., 1981. J. Biol. Chem. 256:9915-9923; and Sassa, et al., 1983. J. Clin. Invest. 71:625-634), the second enzyme of the heme biosynthetic pathway and has immunosuppressive activity (Tschudy et al., 1982. J. Lab. Clin. Med. 99:526-532).

SUMMARY OF THE INVENTION

It is, therefore, an object of the present invention to provide a method of controlling the incompatibility reaction resulting from grafting of immunocompetent cells into an immunologically unreactive allogeneic host, comprising administering to said host an effective amount of succinylacetone to prevent or ameliorate graft versus host disease.

Other objects and advantages of the present invention will become apparent as the detailed description of the present invention proceeds.

BRIEF DESCRIPTION OF DRAWINGS

These and other objects, features and many of the attendant advantages of the invention will be better understood upon a reading of the following detailed description when considered in connection with the accompanying drawings wherein:

FIG. 2 shows the effect of succinylacetone on growth of lethally irradiated rats receiving syngeneic or allogeneic marrow transplants.

Figure 1:
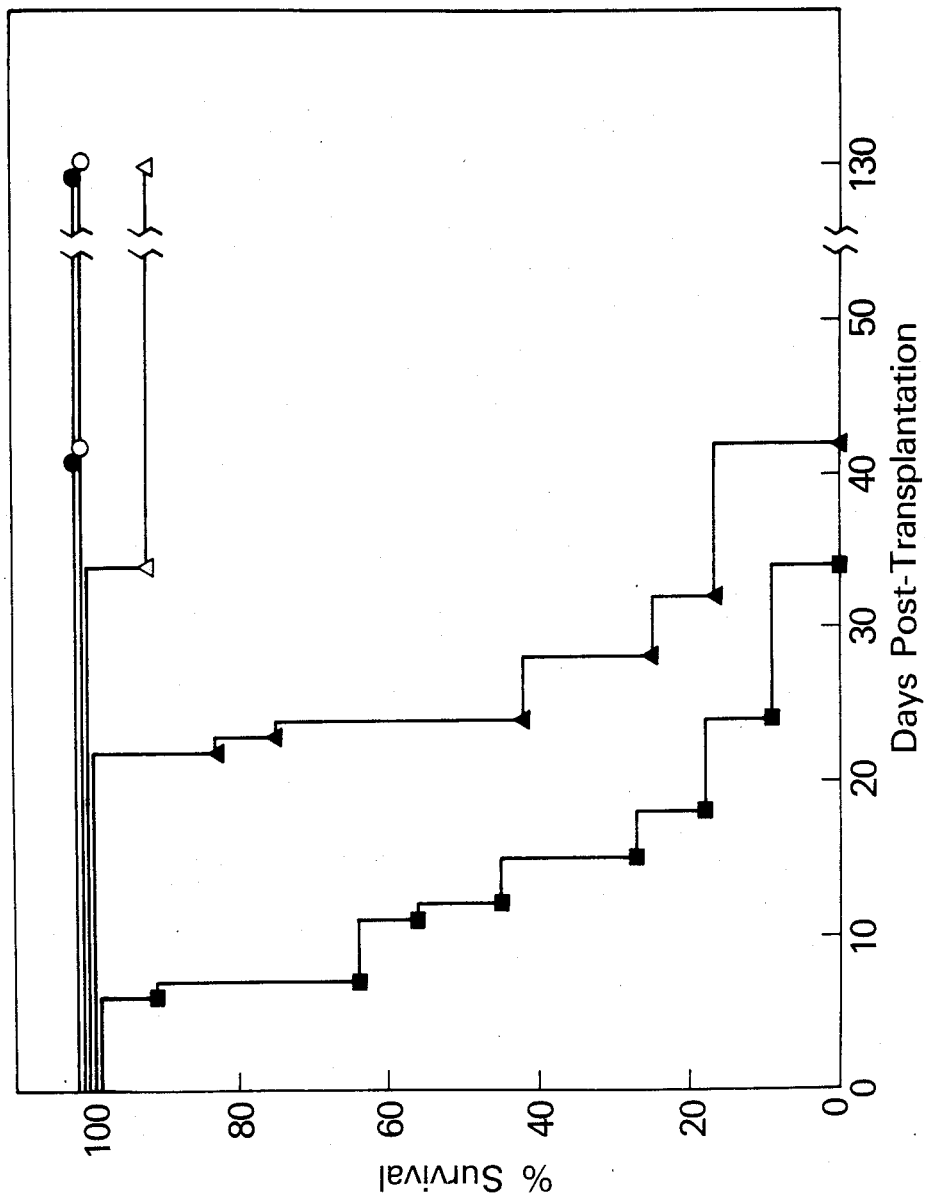
FIG. 1 shows the effect of succinylacetone in the prevention of lethal GVHD caused by allogeneic bone marrow transplantation. The survival curves are composites from three tests, those presented in panels A & B of FIG. 2 and a test which differed from the test in panel A in that $13 \times 10^6$ bone marrow cells and $13 \times 10^6$ spleen cells, approximately one half of the dose in other treatments, were administered, and trimethoprim-sulfamethoxazole was administered for 14 days starting on day 7. ■: radiation controls n=11; ●: syngeneic transplants n=11; ○: syngeneic transplants treated with SA n=6; ▲: allogeneic transplants n=12; △: allogeneic transplants treated with SA n=12.

WF (MHC haplotype $RT1^u$) male rats 200-300 g were exposed to 1000 rads total body radiation in a $Cs^{137}$ small animal irradiator two days after intraperitoneal implantation of two osmotic minipumps (Alza corp.) which delivered about 14 mg/day of succinylacetone (or saline in untreated controls) for 14 days. The concentration of SA in the minipumps was about 600 mg/ml. Four or 5 animals were placed in each of the following groups: ■ irradiated untreated controls: ● irradiated animals given syngeneic marrow ($3 \times 10^7$ cells) and syngeneic spleen ($3 \times 10^7$ cells); ○ syngeneic marrow and spleen cells and treated with SA (osmotic minipumps+subcutaneous administration of SA in corn oil at a dose of about 800 mg/kg every 3-6 days, indicated by vertical arrows ↑); ▲ animals receiving allogeneic (F344 male $RT1^1$) marrow ($3 \times 10^7$ cells) and spleen ($3 \times 10^7$ cells); △ animals given allogeneic bone marrow and spleen cells and treated with SA identically to the SA treated syngeneic group ○ above. Animals were maintained in the "clean" facility of the National Cancer Institute. All animals received gentamicin (3 mg/kg) sc for 10 days after transplantation and trimethoprim (110 mg/1) -sulfamethoxazole (500 mg/1) in the drinking water for 2 weeks after transplantation. The tests presented in panels A and B were performed in identical fashion except for minor differences: a. starting weights differed slightly (207-284 g in panel A, and 250-290 g in panel B); b. syngeneic transplants treated with SA were not studied in panel B test; c. trimethoprim-sulfamethoxazole was not administered in panel B test; d. hematologic reconstitution parameters were measured in panel A test and are presented in Table 1.

DETAILED DESCRIPTION OF INVENTION

The above objects and advantages of the present invention are achieved by a method of controlling GVHD in mammals comprising administering to said mammal an effective amount of succinylacetone (SA) which controls GVHD from developing in said mammal.

The term GVHD as used herein is defined as that condition in a mammal including humans which occurs when allogeneic, immunologically active cells, such as those in bone marrow or spleen, are introduced, transplanted or grafted in a host resulting in a severe, even fatal, reaction due to immunoincompatibility between the host and graft wherein the graft immunologically attacks the host.

Although any similary or equivalent methods and material may be employed in the practice or testing of the present invention, the preferred methods and materials are now described. All publications mentioned hereunder are incorporated herein by reference.

A model for bone marrow transplantation in the rat has previously been described and recent reports have indicated it to be a useful preclinical model for studies of GVHD (Tutschka, in Recent Advances in Bone Marrow Transplantation (ed. Gale) 511–526 Alan R. Liss, New York, 1983). In the present tests the effect of SA on preventing GVHD and its effect on hematologic reconstitution were determined by using treated and untreated Wistar Furth (WF) rats that had received syngeneic (WF) or allogeneic (Fischer 344) bone marrow transplants. To create severe GVHD in recipients of allogeneic cells, equal numbers of spleen cells and bone marrow cells were transplanted intraveneously (i.v.) to lethally irradiated rats.

Hematologic parameters in control and SA treated rats after syngeneic and allogeneic bone marrow transplantation:

Measurements were performed on approximately 1.5 ml of venous blood collected in tubes containing 6 mg of EDTA (ethylenediaminetetraacetic acid). Total leukocyte and erythrocyte counts were determined in a Coulter Counter and platelets by visual microscopy in a Neubauer hemocytometer. Group designations as presented in Table 1 or in FIGS. 1 and 2 are: S=syngeneic transplant, S+SA=syngeneic transplant plus SA treatment, A=allogeneic transplant, A+SA=allogeneic transplant plus SA treatment, R=radiation control. Test 1 is the same test as presented in panel A of FIG. 1. Test 2 differed from test 1 in that a lower dose (approximately half) of marrow and spleen cells was administered ($13 \times 10^6$ marrow and $13 \times 10^6$ spleen cells). Each value represents the mean of measurements on 2 to 4 animals except for day 0 in experiment 2 where n=12. PMNL=poly-morphonuclearleukocytes; NRBC=nucleated red blood cells. The effective dosage of SA ranges from about 600–1000 mg/kg body weight administered every 3–6 days, the preferred dosage being about 800 mg/kg body weight every 4 days. Of course, the dosage may also be adjusted for per diem use as one of ordinary skill in the art can readily determine. The survival curves are presented in FIG. 1 and the weight curves are presented in panels A and B of FIG. 2. In all tests, all untreated irradiated controls died (median survival=12 days). Animals that were given syngeneic transplants with or without SA all survived, although SA treated animals weighed slightly less than untreated animals. All animals given allogeneic transplants and not treated with SA developed lethal GVHD and exhibited profound weight loss, along with variable degrees of alopecia and dermatitis, hunched stature and general unkempt appearance. In contrast, allogeneically transplanted animals given SA over a 26 day period had a 92% (11 of 12) long term survival rate. One of the 12 from this group exhibited some hair loss and failure to gain weight temporarily, and a second animal manifested the same findings over a longer period of time and may have had mild chronic GVHD. All of the other SA treated allogeneically reconstituted animals never exhibited any evidence of GVHD for 7 to 11 months after transplantation, although the curves in FIG. 2 show them to weigh less than syngeneically transplanted animals.

TABLE 1

| | S | S + SA | A | A + SA | R | S | S + SA | A | A + SA | R |
|---|---|---|---|---|---|---|---|---|---|---|
| Experiment 1 | Day 0 | | Day 7 | | | | | Day 13 | | |
| Hemoglobin g/dl | 14.2 | 13.1 | 11.1 | 12.3 | 14.0 | 12.7 | 8.3 | 5.2 | 13.1 | 10.4 | 2.7 |
| Hematocrit % | 39.3 | 34.5 | 36.8 | 33.3 | 37.0 | 32.0 | 24.0 | 14.5 | 36.0 | 29.5 | 7.7 |
| Erythrocytes + $10^6/\mu l$ | 6.52 | 6.42 | 5.92 | 5.54 | 6.88 | 6.51 | 4.04 | 2.60 | 5.78 | 5.38 | 1.44 |
| Lymphocytes + $10^3/\mu l$ | 17.4 | 1 | 1 | 1 | 1 | 1 | 3.3 | 1.8 | 2.1 | 2.0 | 1 |
| PMNL + $10^3/\mu l$ | 2.8 | 1 | 1 | 1 | 1 | 1 | 1.6 | 0.6 | 9.5 | 13.1 | 1 |
| Platelets + $10^3/\mu l$ | 349.0 | 8.6 | 21.4 | 19.0 | 14.1 | 19.2 | 151.0 | 106.0 | 207.0 | 353.0 | 3.8 |
| NRBC + $10^3/\mu l$ | 0.2 | 1 | 1 | 1 | 1 | 1 | 10.0 | 10.2 | 0.8 | 1.3 | 1 |
| Leukocytes + $10^3/\mu l$ | 20.6 | 0.7 | 1.2 | 1.1 | 0.5 | 0.2 | 5.2 | 2.5 | 11.8 | 16.0 | 0.7 |
| Experiment 1 | Day 0 | | Day 28 | | | | | Day 70 | | |
| Hemoglobin g/dl | 14.2 | 14.4 | 12.9 | 3 | 14.2 | | 14.2 | 14.5 | | 15.3 | |
| Hematocrit % | 39.3 | 40.0 | 34.5 | 3 | 39.3 | | 42.1 | 41.0 | | 43.7 | |
| Erythrocytes + $10^6/\mu l$ | 6.52 | 5.93 | 5.34 | 3 | 6.78 | | 7.07 | 6.92 | | 7.12 | |
| Lymphocytes + $10^3/\mu l$ | 17.4 | 4.7 | 3.4 | 3 | 3.0 | | 11.4 | 10.7 | | 5.7 | |
| PMNL + $10^3/\mu l$ | 2.8 | 0.6 | 0.8 | 3 | 3.6 | | 1.87 | 2.2 | | 2.6 | |
| Platelets + $10^3/\mu l$ | 349.0 | 347.0 | 454.0 | 3 | 804.0 | | 250.0 | 266.0 | | 658.0 | |
| NRBC + $10^3/\mu l$ | 0.2 | 16.2 | 35.4 | 3 | 0.2 | | 5.1 | 3.8 | | 0 | |
| Leukocytes + $10^3/\mu l$ | 20.6 | 5.6 | 4.2 | 3 | 6.9 | | 13.8 | 13.6 | | 8.7 | |
| Experiment 2 | Day 0 | | Day 7 | | | | | Day 14 | | |
| Hemoglobin g/dl | 15.4 | 13.6 | 13.3 | 13.7 | 12.4 | 2 | 5.9 | 7.4 | 8.3 | 7.1 | 2 |
| Hematocrit % | 43.5 | 34.5 | 37.5 | 37.0 | 34.5 | 2 | 15.8 | 20.5 | 24.0 | 20.3 | 2 |
| Erythrocytes + $10^6/\mu l$ | 7.43 | 5.85 | 7.11 | 6.67 | 5.04 | 2 | 2.50 | 3.35 | 3.73 | 3.36 | 2 |
| Lymphocytes + $10^3/\mu l$ | 14.3 | 1 | 1 | 1 | 1 | 2 | 1.4 | 2.5 | 2.3 | 4.6 | 2 |
| PMNL + $10^3/\mu l$ | 1.8 | 1 | 1 | 1 | 1 | 2 | 0.7 | 1.9 | 5.7 | 17.0 | 2 |
| Platelets + $10^3/\mu l$ | 328.0 | — | — | — | — | 2 | 367.0 | 74.0 | 85.0 | 193.0 | 2 |
| NRBC + $10^3/\mu l$ | 5.5 | 1 | 1 | 1 | 1 | 2 | 6.8 | 7.6 | 0.8 | 0.9 | 2 |

TABLE 1-continued

|  | S | S + SA | A | A + SA | R | S | S + SA | A | A + SA | R |
|---|---|---|---|---|---|---|---|---|---|---|
| Leukocytes + 10³/μl | 16.6 | 0.8 | 1.8 | 0.4 | 0.5 | 2 | 2.1 | 4.9 | 8.0 | 22.7 | 2 |
| Experiment 2 | Day 0 | | Day 28 | | | | Day 95 | | | |
| Hemoglobin g/dl | 15.4 | 13.3 | 13.6 | 11.8 | 14.0 | | 16.4 | 16.2 | | 17.4 | |
| Hematocrit % | 43.5 | 38.5 | 37.5 | 32.5 | 38.5 | | 45.5 | 43.5 | | 45.0 | |
| Erythrocytes + 10⁶/μl | 7.43 | 5.63 | 6.24 | 4.55 | 6.17 | | 6.95 | 6.98 | | 7.15 | |
| Lymphocytes + 10³/μl | 14.3 | 5.2 | 6.1 | 6.6 | 2.7 | | 15.7 | 18.4 | | 4.4 | |
| PMNL + 10³/μl | 1.8 | 1.5 | 1.2 | 9.6 | 4.8 | | 3.3 | 3.6 | | 3.9 | |
| Platelets + 10³/μl | 328.0 | 374.0 | 370.0 | 469.0 | 602.0 | | 201.0 | 164.0 | | 701.0 | |
| NRBC + 10³/μl | 5.5 | 22.0 | 22.8 | 2.2 | 0.7 | | 0.1 | 1.1 | | 0.1 | |
| Leukocytes + 10³/μl | 16.6 | 6.7 | 7.5 | 16.5 | 7.8 | | 19.2 | 22.2 | | 8.7 | |

[1] Too few to count in differential.
[2] Radiation control rats all dead by Day 7 in this experiment.
[3] Allogeneic reconstituted rats dead by Day 28 this experiment.

The data in Table 1 demonstrate that SA does not interfere with hematologic reconstitution in syngeneic or allogeneic transplant recipients. The complete recovery of red cell numbers and reestablishment of normal hematocrit and hemoglobin indicates that although SA is a potent inhibitor of ALA dehydrase, and thus potentially an inhibitor of heme biosynthesis, it did not prevent engraftment of red cell precursors nor significantly alter the course of red cell reconstitution. The lymphocyte count is lower in SA treated allogeneic transplant recipients than in syngeneic transplant recipients after 4 weeks, but this difference is not attributable to SA. There was no significant difference in the lymphocyte count between SA treated and untreated recipients of syngeneic cells.

Histologic examination of bone marrow and other organs was performed on an animal which had received a syngeneic bone marrow transplant and was treated with SA for 26 days post transplantation. Bone marrow histology on day 295 after marrow transplantation showed normal marrow cellularity with the presence of all elements. Thus the data in Table 1 on both syngeneic and allogeneic grafts and the histological data on syngeneic grafts demonstrate that SA was not toxic to graft cells, did not prevent engraftment and did not significantly alter the rapid growth required of the graft.

The recipients of the bone marrow transplants were shown to be chimeras by the use of standard histocompatability antigen serologic testing (Arn, et al., J. Immun. Meth. 55:141-153; 1982). At 82 to 255 days post reconstitution, cytotoxicity typing showed peripheral leukocytes of SA treated allogeneically reconstituted rats (F344→WF) to be 93±6% F344 cells (normal F344 were 101±5%).

In the rat bone marrow transplant system, SA exhibited great advantage over previously described effect of cyclosporin A, which upon withdrawal was followed by GVHD not only in allogeneic transplants but also in syngeneic transplants (Glazier, et al., Transplantation Proceedings 15, Suppl. 1:3035-3041; 1983). This phenomenon did not occur with SA. Thus, the results presented herein demonstrate that SA treatment for 26 days (a) converted the mortality rate of allogeneic bone marrow and spleen cell transplants from 100% to 8%; (b) allowed hematologic reconstitution; and (c) allowed long term survival with weight gain. The surprising efficacy of SA as disclosed herein for the control and prevention of GVHD is, therefore, remarkable. Of course, the data presented herein also indicate advantageous application and utility of SA in other transplant or graft procedures or in disease states wherein immunologically active cells may be involved, in graft rejection or in autoimmune disease and the like.

The method or route of administering SA in the host is not critical but the preferred route is subcutaneous injection in conjunction with or without osmotic minipumps.

It is understood that the examples and embodiments described herein are for illustrative purposes only and that various modifications or changes in light thereof will be suggested to persons skilled in the art and are to be included within the spirit and purview of this application and the scope of the appended claims.

We claim:

1. A method of controlling the incompatibility reaction resulting from grafting of immunocompetent cells into an immunologically unreactive allogeneic host, comprising adminstering to said host an effective amount of succinylacetone to prevent or ameliorate graft versus host disease caused by implanting of bone marrow cells.

2. The method of claim 1 wherein the amount of succinylacetone is about 600–1000 mg/kg body weight every 3 to 6 days.

3. The method of claim 2 wherein the amount is 800 mg/kg body weight every 4 days.

4. The method of claim 3 wherein succinylacetone is administered subcutaneously or by osmotic minipumps.

5. The method of claim 4 wherein succinylactone is administered as an aqueous solution or oil suspension.

* * * * *